United States Patent
Fu et al.

(10) Patent No.: US 8,154,723 B2
(45) Date of Patent: Apr. 10, 2012

(54) METHOD AND SYSTEMS FOR PARTICLE CHARACTERIZATION USING OPTICAL SENSOR OUTPUT SIGNAL FLUCTUATION

(75) Inventors: Yongji Fu, Aloha, OR (US); Deepak Ayyagari, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 282 days.

(21) Appl. No.: 12/384,368

(22) Filed: Apr. 3, 2009

(65) Prior Publication Data

US 2010/0253943 A1   Oct. 7, 2010

(51) Int. Cl.
*G01N 15/02* (2006.01)
*G01N 21/00* (2006.01)

(52) U.S. Cl. .................. 356/335; 356/336; 356/338

(58) Field of Classification Search ........... 356/335–344
See application file for complete search history.

(56) References Cited

U.S. PATENT DOCUMENTS

| | | | | |
|---|---|---|---|---|
| 3,830,568 A * | 8/1974 | Allen | | 356/28 |
| 4,279,512 A * | 7/1981 | Tunstall | | 356/335 |
| 4,448,680 A * | 5/1984 | Wilks et al. | | 209/564 |
| 5,135,306 A * | 8/1992 | Kanebako et al. | | 356/336 |
| 5,619,324 A | 4/1997 | Harvill et al. | | 356/336 |
| 5,784,160 A * | 7/1998 | Naqwi | | 356/496 |
| 6,011,621 A | 1/2000 | Marijnissen et al. | | 356/336 |
| 6,119,510 A * | 9/2000 | Carasso et al. | | 73/61.75 |
| 6,525,807 B1 | 2/2003 | Morikawa et al. | | 356/72 |
| 6,525,823 B1 | 2/2003 | Dogariu | | 356/479 |
| 7,122,384 B2 | 10/2006 | Prober et al. | | 436/524 |
| 7,127,356 B2 | 10/2006 | Nicoli et al. | | 702/26 |
| 7,230,698 B2 | 6/2007 | Kurozumi et al. | | 356/336 |
| 7,302,313 B2 | 11/2007 | Sharp et al. | | 700/276 |
| 7,471,393 B2 * | 12/2008 | Trainer | | 356/336 |
| 2004/0233431 A1 * | 11/2004 | Ganz et al. | | 356/338 |
| 2008/0221711 A1 * | 9/2008 | Trainer | | 700/54 |

FOREIGN PATENT DOCUMENTS

JP   4-052550 A   2/1992
JP   2003-254888   9/2003

OTHER PUBLICATIONS

Sharp Corporation, "Device Specification for Air Quality Sensor Model No. GP2Y1010AU," 2002, 12 pages.
R. Weber et al., "Analysis of a Flowing Aerosol by Correlation Spectroscopy. Concentration, Aperture, Velocity and Particle Size Effects," J. Aerosol Sci., 1993, vol. 24, No. 4, pp. 485-499.

* cited by examiner

*Primary Examiner* — Gregory J Toatley
*Assistant Examiner* — Jarreas C Underwood
(74) *Attorney, Agent, or Firm* — Scot A. Reader

(57) ABSTRACT

Methods and systems for particle characterization using a light fluctuation component of an optical sensor output signal. The use of the light fluctuation component enables particle characterization (e.g. provision of information on particle size, type and confidence) without requiring measurements at multiple wavelengths or multiple angles and using relatively lightweight calculations. The methods and systems allow integration of real-time airborne particle characterization into portable monitors. The methods and systems in some embodiments also use the output signal to further characterize particles through determination of particle density information.

12 Claims, 7 Drawing Sheets

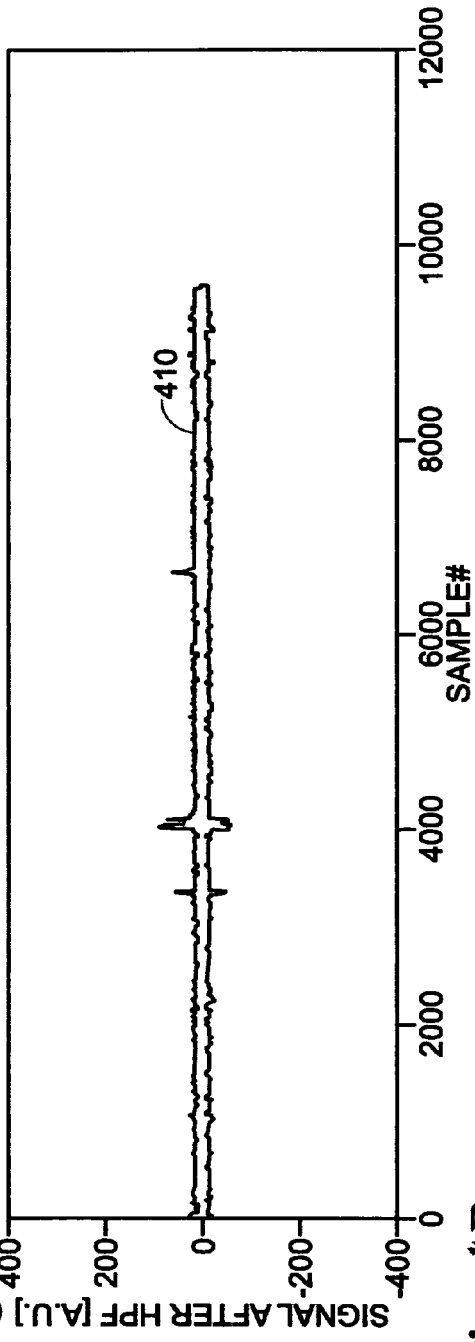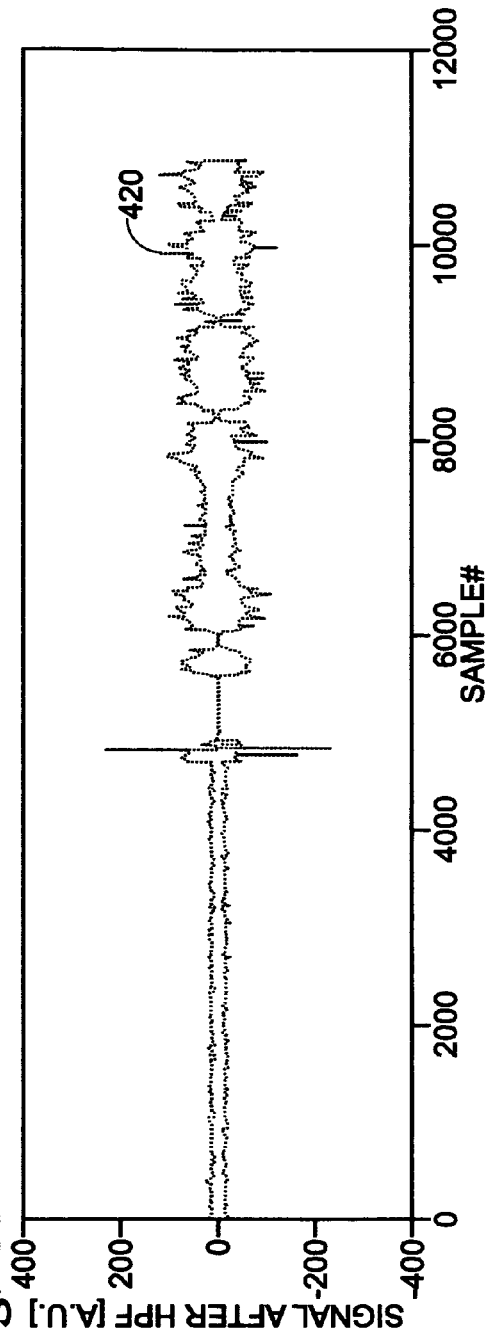

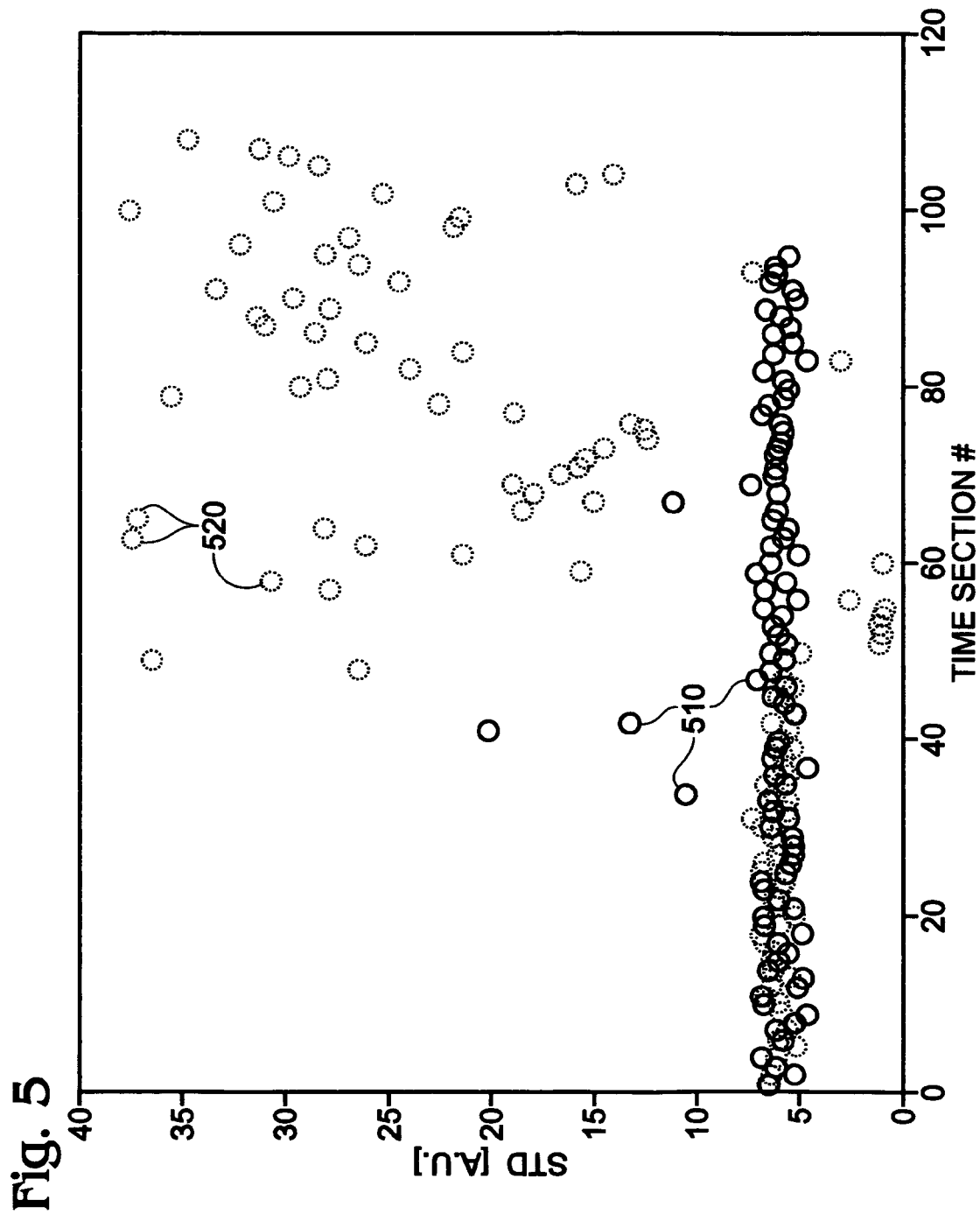

METHOD AND SYSTEMS FOR PARTICLE CHARACTERIZATION USING OPTICAL SENSOR OUTPUT SIGNAL FLUCTUATION

BACKGROUND OF THE INVENTION

The present invention relates to characterization of particles and, more particularly, to methods and systems for particle characterization using an optical sensor output signal.

Particle sensing has many applications. One application is respiratory disease alerts. Exposure to airborne particles is closely associated with respiratory ailments, such as asthma, bronchitis and respiratory infections. Thus, early detection and alerting of a patient of airborne particles can allow the patient to take a respiratory health-preserving action (e.g. evacuation of an area with high particle density) and reduce the incidence and severity of respiratory afflictions. Other applications for particle sensing include biological cell identification, worker protection in dusty environments and ocean water analysis.

Portable monitors that sense and report in real-time on the presence of airborne particles in the vicinity of a patient are known. These portable monitors often take continual light scattering measurements that detect the presence of airborne particles and notify the patient who is wearing the monitor of particle presence. While such portable monitors inform about the presence of airborne particles, they are not known to characterize airborne particles, such as by providing information on particle density, size and type. The lack of airborne particle characterization leaves the patient and his or her health care provider without information required to make optimal respiratory health-preserving decisions. For example, for a given respiratory disease or patient, a different health-preserving action may be indicated depending on the type of a detected particle (e.g. smoke, dust, pollen, etc.) or whether the detected particle is large or small.

Advanced optical sensors that characterize airborne particles are known. These advanced sensors often take light scattering measurements at multiple wavelengths and/or multiple angles to generate a large body of scattered light data. The body of light scattering data is then applied to a database to obtain fitted results concerning particle size and/or type. Accordingly, these advanced sensors require substantial overhead and are typically not suitable for use in portable monitors.

SUMMARY OF THE INVENTION

The present invention, in a basic feature, provides methods and systems for particle characterization using a light fluctuation component of an optical sensor output signal. The use of the light fluctuation component in the methods and systems of the present invention enable particle characterization (e.g. provision of information on particle size, type and confidence) without requiring measurements at multiple wavelengths or multiple angles and using relatively lightweight calculations. The present methods and systems thereby allow integration of real-time airborne particle characterization into portable monitors. The present invention in some embodiments also uses the output signal to further characterize particles through determination of particle density information.

In one aspect of the invention, a system for particle characterization comprises a signal processor and an optical sensor communicatively coupled with the signal processor, wherein the signal processor isolates a light fluctuation component of an output signal received from the optical sensor and determines particle size information using the light fluctuation component.

In some embodiments, the system further comprises an output interface communicatively coupled with the signal processor, wherein the signal processor transmits the particle size information to the output interface, whereon the particle size information is displayed.

In some embodiments, the signal processor further determines particle type information using the light fluctuation component.

In some embodiments, the signal processor further determines a confidence index for the particle type information using at least one predetermined profile.

In some embodiments, the signal processor further determines particle density information using the output signal.

In some embodiments, the signal processor isolates the light fluctuation component at least in part by applying a high pass filter to the output signal.

In some embodiments, the signal processor determines at least one standard deviation of the light fluctuation component and compares the standard deviation with at least one standard deviation threshold associated with a particle size to determine the particle size information.

In some embodiments, the signal processor determines at least one standard deviation of the light fluctuation component and compares the standard deviation with at least one standard deviation profile associated with a particle type to determine the particle type information.

In another aspect of the invention, a system for particle characterization comprises a signal processor and an optical sensor communicatively coupled with the signal processor, wherein the signal processor isolates a light fluctuation component of an output signal received from the optical sensor and determines particle type information using the light fluctuation component.

In some embodiments, the system further comprises an output interface communicatively coupled with the signal processor, wherein the signal processor transmits the particle type information to the output interface, whereon the particle type information is displayed.

In some embodiments, the signal processor further determines a confidence index for the particle type information using the light fluctuation component and a predetermined profile.

In some embodiments, the signal processor determines at least one standard deviation of the light fluctuation component and compares the standard deviation with at least one standard deviation profile associated with a particle type to determine the particle type information.

In yet another aspect of the invention, a method for particle characterization comprises the steps of receiving an output signal from an optical sensor, isolating a light fluctuation component of the output signal, characterizing a particle using the light fluctuation component and displaying particle information determined in the characterizing step on an output interface.

In some embodiments, the particle information comprises particle size information.

In some embodiments, the particle information comprises particle type information.

In some embodiments, the particle information comprises confidence information associated with the particle type information.

In some embodiments, the particle information comprises particle density information.

In some embodiments, the isolating step comprises applying a high pass filter to the output signal.

In some embodiments, the characterizing step comprises the substeps of determining at least one standard deviation of the light fluctuation component and comparing the standard deviation with at least one standard deviation threshold associated with a particle size.

In some embodiments, the characterizing step comprises the substeps of determining at least one standard deviation of the light fluctuation component and comparing the standard deviation with at least one standard deviation profile associated with a particle type.

These and other aspects of the invention will be better understood by reference to the following detailed description taken in conjunction with the drawings that are briefly described below. Of course, the invention is defined by the appended claims.

BRIEF DESCRIPTION OF THE DRAWINGS

FIG. 4A shows a light fluctuation component of the output signal of FIG. 2 across the smoke sampling regime isolated through application of a high pass filter to the output signal.

FIG. 4B shows a fluctuation component of the output signal of FIG. 2 across the dust sampling regime isolated through application of a high pass filter to the output signal.

FIG. 5 shows standard deviations of the light fluctuation components of FIGS. 4A and 4B, respectively, for different time sections.

DETAILED DESCRIPTION OF A PREFERRED EMBODIMENT

Figure 1:
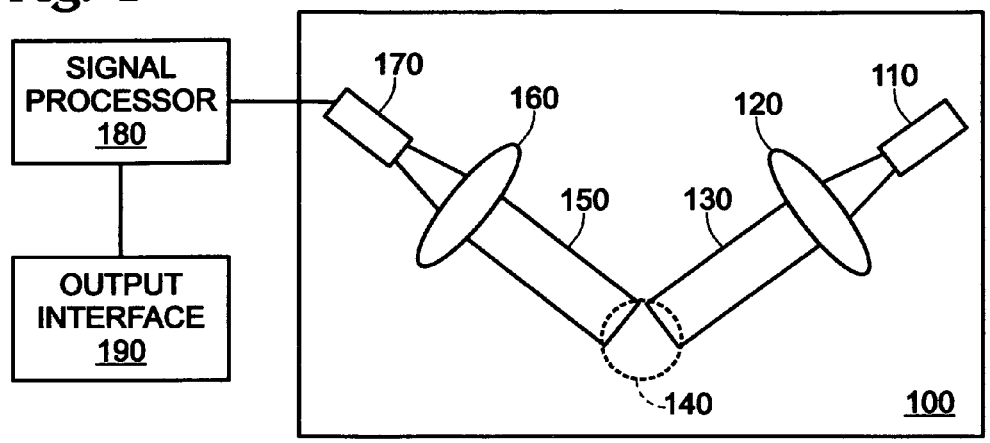
FIG. 1 shows a system for particle detection and characterization.

FIG. 1 shows an airborne particle detection and characterization system in some embodiments of the invention. The system may be integrated into a portable monitor worn by a patient, for example. The system includes a signal processor 180 communicatively coupled between an optical sensor 100 and an output interface 190. Optical sensor 100 has a light source 110, such as a light emitting diode (LED), that provides incident light to a first lens 120. First lens 120 collimates the incident light to produce collimated light 130. The collimated light 130 is scattered by particles in a light scattering region 140 to produce scattered light 150 that is indicative of particle presence in light scattering region 140. The scattered light 150 passes through a second lens 160 and is recorded by an optical detector 170 that converts the recorded light into a voltage. Optical detector 170 transmits to signal processor 180 an output signal that is proportional to the voltage. After performing an analog-to-digital conversion, signal processor 180 isolates a light fluctuation component of the output signal and uses the light fluctuation component to characterize particles within light scattering region 140, including generating one or more of particle density, size, type and confidence information. Signal processor 180 transmits the particle characterization information to output interface 190. In some embodiments, output interface has a display screen, such as a liquid crystal display (LCD) screen or a light emitting diode (LED) display screen for displaying the information to a user of the system, such as an asthma patient or a respiratory health professional. In some embodiments, optical sensor 100, signal processor 180 and output interface 190 are collocated on a single device, such as a portable environmental monitor worn by a user. In other embodiments, sensor 100, processor 180 and interface 190 are distributed across multiple devices that communicate via wired and/or wireless connections. Moreover, functions described herein as performed by a particular one of elements 100, 180, 190 may be performed on a single device or distributed across multiple devices.

Figure 2:
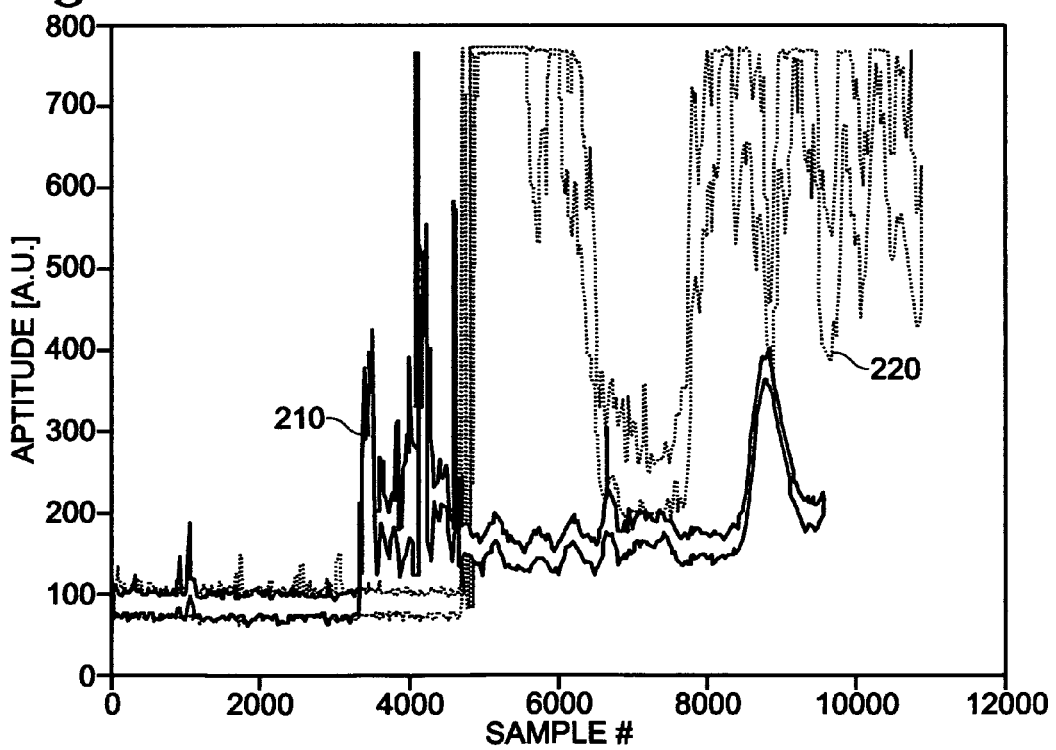
FIG. 2 shows exemplary output signals from an optical sensor across a smoke sampling regime and a dust sampling regime, respectively.

FIG. 2 shows exemplary output signals 210, 220 from optical sensor 100 across an incense smoke (200-300 nm) sampling regime and an Arizona dust (10-20 μm) sampling regime, respectively. In the example shown, the smoke and dust sampling were performed at different times, but the resultant smoke output signal 210 and dust output signal 220 are displayed on the same chart for illustrative purposes.

During both sampling instances, optical sensor 100 and signal processor 180 were disposed in a closed air chamber and the sampling frequency was 100 Hz. The chart shows the "aptitude" in "aptitude units" (A.U.) for output signals 210 (incense smoke), 220 (Arizona dust) from optical sensor 100 as a function of sample number. The aptitude is proportional to the recorded light intensity voltage generated by optical detector 170.

Continuing with FIG. 2, in the smoke sampling, incense smoke consisting of fine particles in the 200 to 300 nanometer aerodynamic diameter range was introduced in light scattering region 140 at about sample number 3300, resulting in a measurable increase in the aptitude of output signal 210 through the end of the sampling regime (at about sample number 9500). In the dust sampling, Arizona dust consisting of large particles in the 10 to 20 micrometer aerodynamic diameter range was introduced in light scattering region 140 at about sample number 4800, resulting in a measurable increase in the aptitude of output signal 220 through the end of the sampling regime (at about sample number 11,000). The time when particles were present in light scattering region 140 is ascertainable by reference to the aptitude of output signals 210, 220. However, the fine smoke particles and large dust particles are not readily distinguishable from one another, and particle characterization information such as particle size and type is not ascertainable by reference to the aptitude of signals 210, 220 alone. Accordingly, in an important feature of the invention, a light fluctuation component of each of signals 210, 220 is isolated to enable the fine smoke particles and large dust particles to be distinguished and particle characterization information to be ascertained.

Figure 3A:
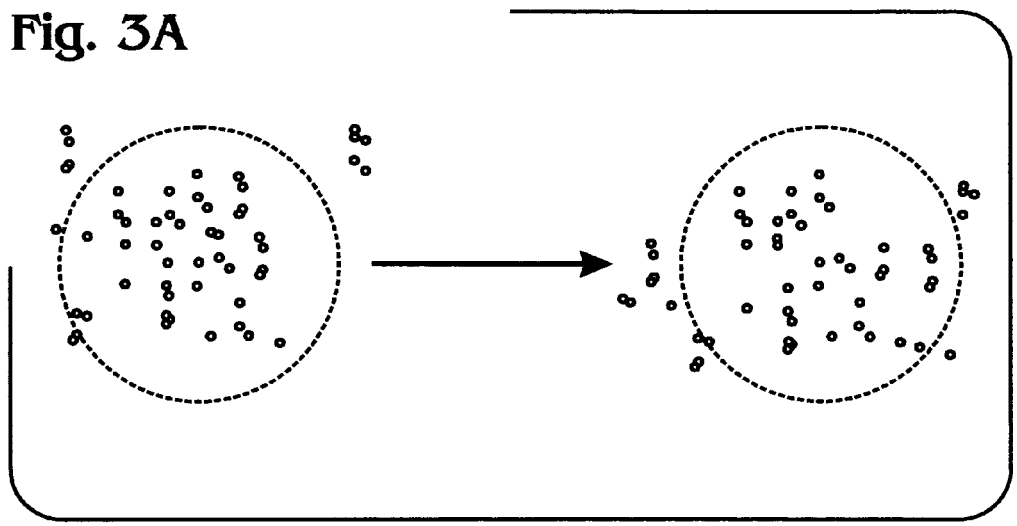
FIG. 3A illustrates particle drift over time in a light scattering region during a period of stable smoke concentration.
Figure 3B:
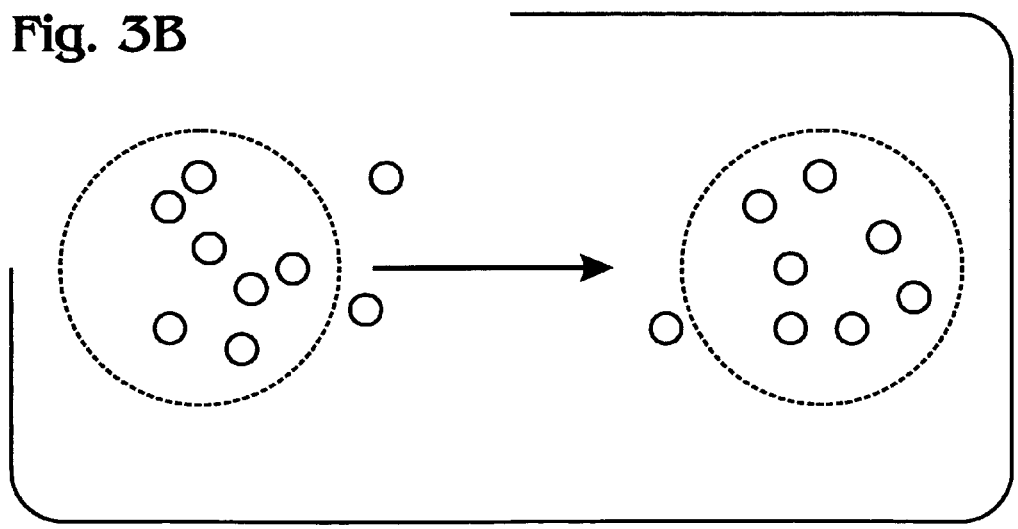
FIG. 3B illustrates particle drift over time in a light scattering region during a period of stable dust concentration.

The principle of light fluctuation is illustrated by reference to FIGS. 3A and 3B. FIG. 3A and FIG. 3B illustrate particle drift in light scattering region 140 during a period of stable smoke concentration and stable dust concentration, respectively. Referring first to FIG. 3A, during a period of stable smoke concentration, the shift of fine smoke particles in and around light scattering region 140 between a first time and a second time results in a low change in particle density and low fluctuation of scattered light that will be recorded by optical detector 170. Referring next to FIG. 3B, during a period of stable dust concentration, the shift of large dust particles in and around light scattering region 140 between a first time and a second time results in a similarly low change in particle density; however, due to the larger size of the dust particles, this shift results in a relatively high fluctuation of scattered light that will be recorded by optical detector 170. A high pass filter is thus applied to output signals 210 220 to filter the slow-changing density component of signals 210, 220 and isolate the light fluctuation component of signals 210, 220 that enables the fine smoke particles and large dust particles to be distinguished and particle characterization information to be ascertained.

FIGS. 4A and 4B show light fluctuation components 410, 420 extracted from output signals 210, 220, respectively, through application of a high pass filter to output signals 210, 220, respectively. In the illustrated example, the high pass filter is a 30 Hz high pass filter applied by signal processor 180. Referring first to FIG. 4A, application of the high pass filter to output signal 210 associated with fine smoke particles reveals a light fluctuation component 410 that is stable, reflecting the relatively low fluctuation of scattered light from drift of the fine smoke particles in light scattering region 140. Referring next to FIG. 4B, application of the high pass filter to output signal 220 associated with large dust particles reveals a light fluctuation component 420 that is relatively unstable, reflecting the relatively high fluctuation of scattered light from drift of the large dust particles in light scattering region 140. Application of the high pass filter enables the fine smoke particles and large dust particles to be distinguished and particle characterization information to be ascertained in a manner now described in greater detail.

First, for each sampling regime, standard deviations of the light fluctuation component are calculated for each time section. FIG. 5 provides a chart showing standard deviations 510, 520 calculated for time sections of light fluctuation components 410, 420, respectively. Each time section represents one second of sampling such that each data point represents a standard deviation of 100 contiguous samples.

Next, for each sampling regime, the calculated standard deviations are compared with at least one configured standard deviation threshold associated with a particle size to classify the particles detected in each time section into a size category (e.g. small, medium, large). In FIG. 5, the standard deviations are plotted in aptitude units. Strictly way of example, a standard deviation of greater than 20 aptitude units may indicate that particles detected within a time section are large, a standard deviation of between 20 and 15 aptitude units may indicate that particles detected within a time section are medium, a standard deviation of between 15 and 10 aptitude units may indicate that particles within a time section are small (fine) and a standard deviation of less than 10 aptitude units may indicate indeterminate particle size. Applying these standard deviation thresholds to the standard deviation data points plotted in FIG. 5, the smoke particles represented by standard deviations 510 are most often classified as "small" and the dust particles represented by standard deviations 520 are most often classified as "large."

Next, for each sampling regime, one or more calculated standard deviations are compared with at least one predetermined standard deviation profile associated with a particle type to identify a type of particles detected in the sampling regime and a confidence index for the type identification. One or more standard deviations 510 are compared with standard deviation profiles (and possibly other accepted standard deviation profiles for other particle types, such as pollen, spore, soot, aerosol, etc.) to identify the particles detected in the sampling regime represented by standard deviations 510 as incense smoke particles. Profile comparisons are similarly performed for one or more standard deviations 520 to identify the particles detected in the sampling regime represented by standard deviations 520 as Arizona dust particles. Depending on implementation, a profile comparison may compare instantaneous standard deviations or an average standard deviation with the accepted standard deviation profiles. An accepted standard deviation profile for a given particle type is determined from empirical tests involving the particle type, and may be a single value or may include a range of values. A confidence index is generated based on the quality of the match between standard deviations 510, 520 and matching standard deviation profiles, respectively. The confidence index may be a value between one and five, for example.

Figure 6:
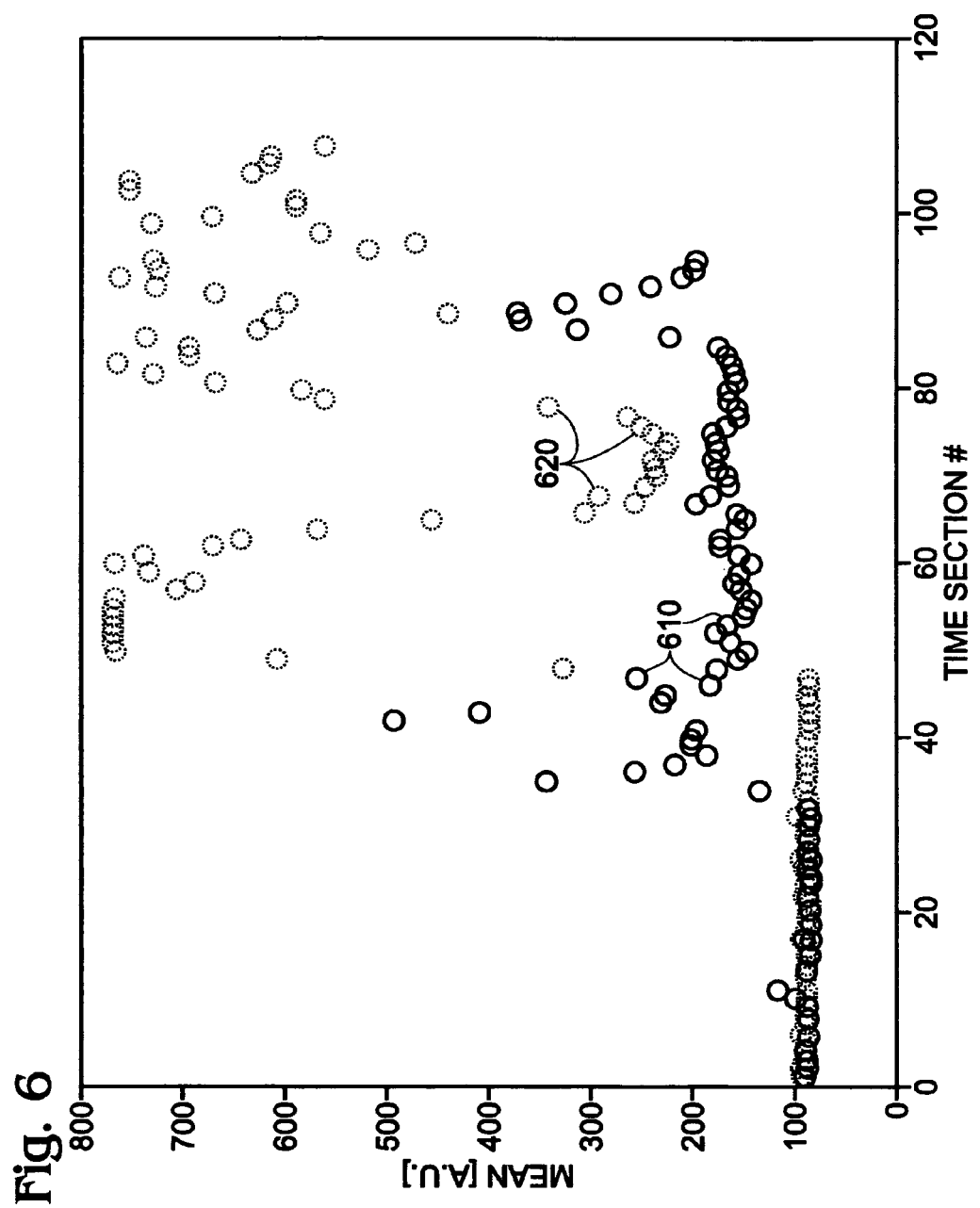
FIG. 6 shows an average (mean) density for a smoke sampling regime and a dust sampling regime, respectively, for different time sections.

FIG. 6 is a chart showing average (mean) density values 610, 620 calculated for a smoke sampling regime and a dust sampling regime, respectively, for different time sections. Each time section represents one second of sampling such that each data point represents average density over 100 contiguous samples.

Figure 7:
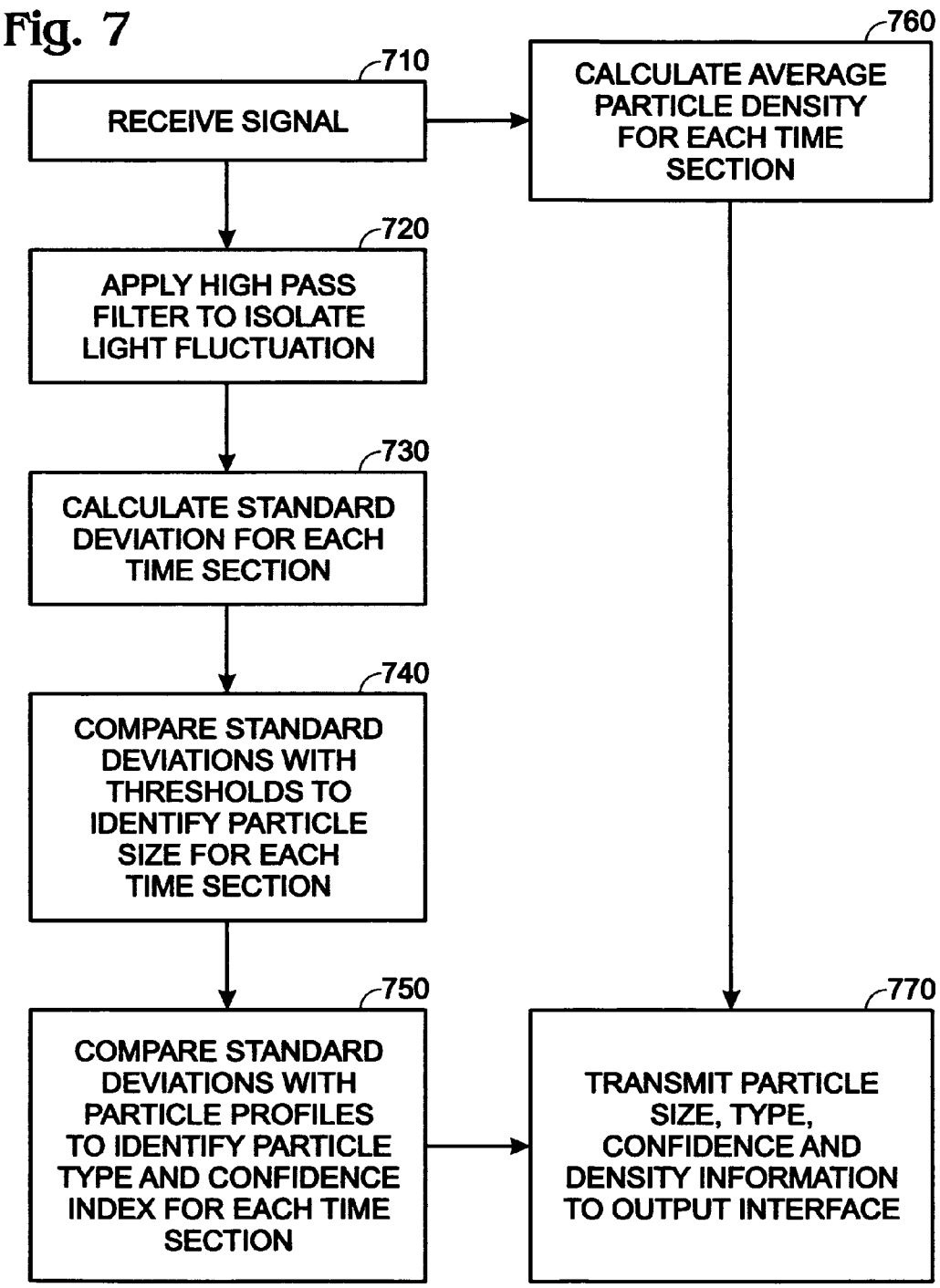
FIG. 7 shows a method for airborne particle characterization using a light fluctuation component of an output signal received from an optical sensor in some embodiments of the invention.

FIG. 7 shows a method for airborne particle characterization using a light fluctuation component of an output signal received from an optical sensor in some embodiments of the invention. Signal processor 180 receives an output signal from optical sensor 100 (710) and applies a high pass filter to the output signal to isolate a light fluctuation component of the output signal (720). Signal processor 180 calculates a standard deviation for each time section of the light fluctuation component (730). Signal processor 180 compares the standard deviation for each time section with standard deviation thresholds for different particle sizes (e.g. small, medium, large) to classify the particles detected in each time section into a particle size category (740). Signal processor 180 also compares the standard deviations of one or more time sections with accepted standard deviation profiles for different particle types (e.g. smoke, dust, pollen, spore, soot, aerosol) to identify a type of particle detected and an associated confidence index (750). Signal processor 180 also calculates an average density of particles detected in each time section from the output signal (760). Signal processor 180 transmits the particle density, size, type and confidence information to output interface 190 whereon the particle characterization information is displayed to a user of the particle characterization system (770).

Figure 8:
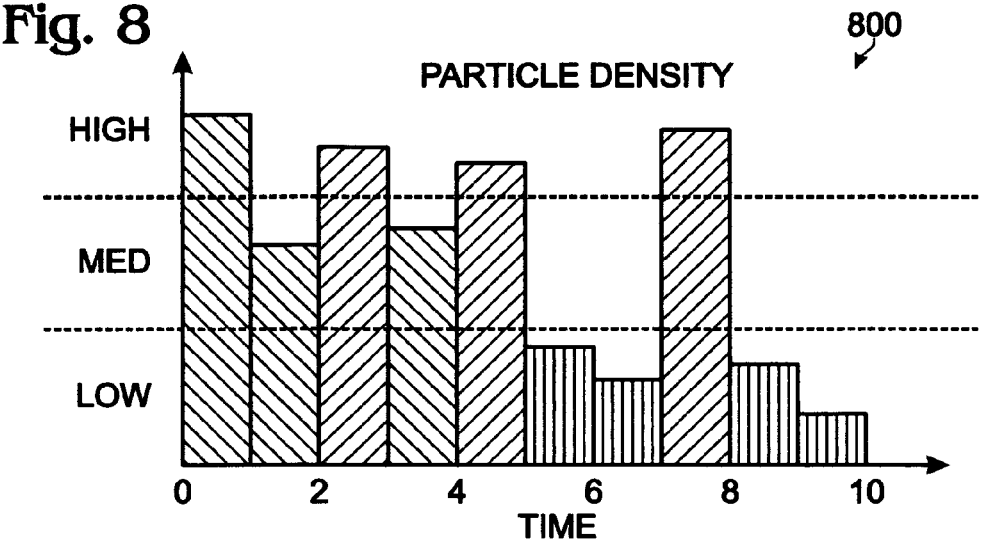
FIG. 8 shows a particle density output display on an output interface in some embodiments of the invention.

FIG. 8 shows a particle density output display 800 on output interface 190 in some embodiments of the invention. Display 800 shows particle density as a function of time in histogram format. The bars of the histogram inform a user of the particle characterization system whether the particle density at different times in a recent time horizon was high, medium or low. In some embodiments, the bars are color-coded (e.g. high=red, medium=yellow, low=green) to convey the particle density information in a user friendly way. Moreover, display 800 may be accompanied by audible or tactile information. For example, at times of high particle density, output interface 190 may sound an alarm or vibrate.

Figure 9:
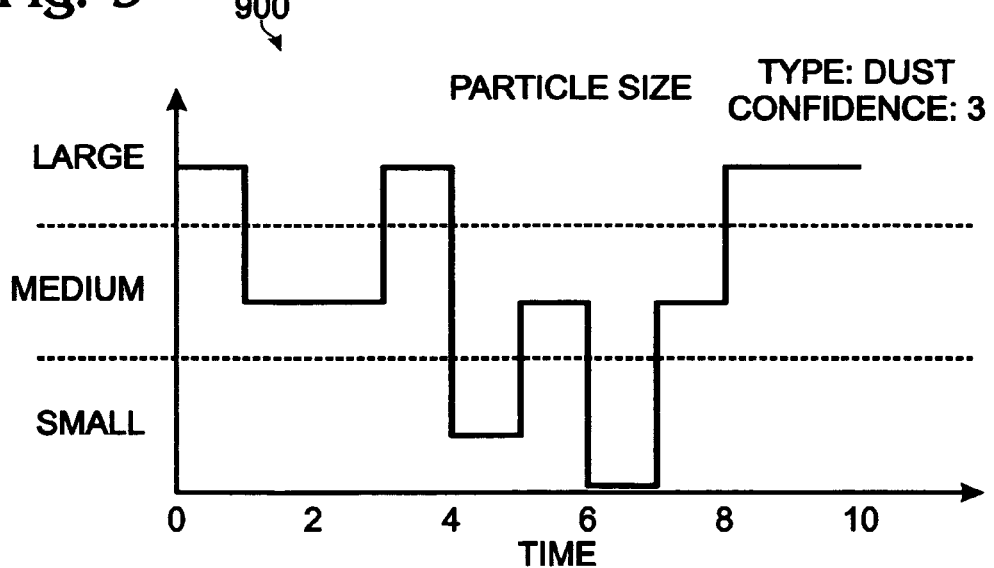
FIG. 9 shows a particle size, type and confidence display on an output interface in some embodiments of the invention.

FIG. 9 shows a particle size, type and confidence display 900 on output interface 190 in some embodiments of the invention. Display 900 shows particle size information as a function of time in a line graph format. The vertical level of the line informs a user of the particle characterization system whether the particle size at different times in a recent time horizon was large, medium, small (fine), or indeterminate.

Particle size may be indeterminate during periods of saturation when the calculated standard deviation of the fluctuation component is near zero, for example. Display 900 also shows in a textual format the particle type at the most recent time and a confidence index as to the correctness of the identified particle type. The confidence index may be, for example, a number between one and five. Moreover, display 900 may be accompanied by audible or tactile information. For example, at times when a particle size or particle type to which a patient has a known sensitivity is detected, output interface 190 may sound an alarm or vibrate.

Functions described herein as being performed by signal processor 180 may be performed using software executable on a microprocessor, custom circuitry or a combination thereof.

It will be appreciated by those of ordinary skill in the art that the invention can be embodied in other specific forms without departing from the spirit or essential character hereof. The present description is therefore considered in all respects to be illustrative and not restrictive. The scope of the invention is indicated by the appended claims, and all changes that come with in the meaning and range of equivalents thereof are intended to be embraced therein.

What is claimed is:

1. A system for particle characterization, comprising:
   a signal processor; and
   an optical sensor communicatively coupled with the signal processor, wherein the signal processor maintains associations between discrete standard deviation ranges and particle size categories representing discrete particle sizes, wherein higher standard deviation ranges are associated with larger particle sizes, and wherein the signal processor isolates a light fluctuation component of an output signal received from the optical sensor, computes a standard deviation of the light fluctuation component from samples taken at different times within a time section and classifies particles detected during the time section into a the particle size category associated with the standard deviation range within which the standard deviation falls.

2. The system of claim 1, further comprising an output interface communicatively coupled with the signal processor, wherein the signal processor transmits the particle size category to the output interface, whereon the particle size category is displayed.

3. The system of claim 1, wherein the signal processor further classifies particles detected during the time section into a particle type category using the standard deviation.

4. The system of claim 3, wherein the signal processor further determines a confidence index for classification into the particle type category using the standard deviation.

5. The system of claim 1, wherein the signal processor further determines particle density information using the output signal.

6. The system of claim 1, wherein the signal processor isolates the light fluctuation component at least in part by applying a high pass filter to the output signal.

7. The system of claim 3, wherein the signal processor compares the standard deviation with at least one standard deviation profile associated with a particle type category to classify the particles into the particle type category.

8. A system for particle characterization, comprising:
   a signal processor; and
   an optical sensor communicatively coupled with the signal processor, wherein the signal processor maintains associations between discrete standard deviation profiles and particle type categories representing discrete airborne contaminants, and wherein the signal processor isolates a light fluctuation component of an output signal received from the optical sensor, computes a standard deviation of the light fluctuation component from samples taken at different times within a time section and classifies particles detected during the time section into the particle type category associated with the standard deviation profile that most closely matches the standard deviation.

9. The system of claim 8, further comprising an output interface communicatively coupled with the signal processor, wherein the signal processor transmits the particle type category to the output interface, whereon the particle type category is displayed.

10. The system of claim 8, wherein the signal processor further determines a confidence index for classification into the particle type category using the standard deviation.

11. A method for particle characterization, comprising the steps of:
    maintaining associations between discrete standard deviation ranges and particle size categories representing discrete particle sizes, wherein higher standard deviation ranges are associated with larger particle sizes;
    receiving an output signal from an optical sensor;
    isolating a light fluctuation component of the output signal;
    computing a standard deviation of the light fluctuation component from samples taken at different times within a time section;
    classifying particles detected during the time section into the particle size category associated with the standard deviation range within which the standard deviation falls; and
    displaying the category on an output interface.

12. The method of claim 11, wherein the isolating step comprises applying a high pass filter to the output signal.

* * * * *

UNITED STATES PATENT AND TRADEMARK OFFICE
CERTIFICATE OF CORRECTION

| | |
|---|---|
| PATENT NO. | : 8,154,723 B2 |
| APPLICATION NO. | : 12/384368 |
| DATED | : April 10, 2012 |
| INVENTOR(S) | : Fu et al. |

It is certified that error appears in the above-identified patent and that said Letters Patent is hereby corrected as shown below:

Cover Page: Item 54 and Col. 1 Line 1

In the Title, "METHOD" is replaced with --METHODS--.

Column 7, Line 39, "into a the particle" is replaced with --into the particle--.

Signed and Sealed this
Twenty-ninth Day of May, 2012

David J. Kappos
*Director of the United States Patent and Trademark Office*